US009657257B2

(12) United States Patent
MacDonald et al.

(10) Patent No.: US 9,657,257 B2
(45) Date of Patent: May 23, 2017

(54) COLORANT NEUTRALIZER

(75) Inventors: John Gavin MacDonald, Decatur, GA (US); Molly K. Smith, Atlanta, GA (US); Shu-Ping Yang, Alpharetta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 123 days.

(21) Appl. No.: 11/801,612

(22) Filed: May 10, 2007

(65) Prior Publication Data

US 2008/0277621 A1 Nov. 13, 2008

(51) Int. Cl.

| | |
|---|---|
| ***C11D 3/00*** | (2006.01) |
| ***C11D 11/00*** | (2006.01) |
| ***A61K 8/22*** | (2006.01) |
| ***A61K 8/36*** | (2006.01) |
| ***A61K 8/39*** | (2006.01) |
| ***A61C 11/00*** | (2006.01) |
| ***A61C 19/02*** | (2006.01) |
| ***C11D 3/20*** | (2006.01) |

(52) U.S. Cl.

CPC .......... *C11D 11/0017* (2013.01); *A61C 11/00* (2013.01); *A61C 19/02* (2013.01); *A61K 8/22* (2013.01); *A61K 8/361* (2013.01); *A61K 8/39* (2013.01); *C11D 3/2079* (2013.01); *C11D 3/2093* (2013.01)

(58) Field of Classification Search

None

See application file for complete search history.

(56) References Cited

U.S. PATENT DOCUMENTS

| | | | | |
|---|---|---|---|---|
| 2,236,529 | A | 4/1941 | Epstein et al. | |
| 2,542,909 | A | 2/1951 | De Wet | |
| 3,635,828 | A | 1/1972 | Benjamin et al. | |
| 3,663,445 | A | 5/1972 | Augustin et al. | |
| 3,953,351 | A | 4/1976 | Keller | |
| 3,979,318 | A | 9/1976 | Tokiwa et al. | |
| 4,259,383 | A | 3/1981 | Eggensperger et al. | |
| 4,288,225 | A | 9/1981 | Roland et al. | |
| 4,431,560 | A | 2/1984 | Lake et al. | |
| 4,585,650 | A * | 4/1986 | Newberry et al. | 424/73 |
| 4,673,524 | A | 6/1987 | Dean | |
| 4,798,603 | A | 1/1989 | Meyer et al. | |
| 4,801,494 | A | 1/1989 | Datta et al. | |
| 4,847,089 | A | 7/1989 | Kramer et al. | |
| 4,886,512 | A | 12/1989 | Damico et al. | |
| 4,908,026 | A | 3/1990 | Sukiennik et al. | |
| 5,009,716 | A | 4/1991 | Gerson | |
| 5,248,309 | A | 9/1993 | Serbiak et al. | |
| 5,262,153 | A | 11/1993 | Mishima et al. | |
| 5,340,493 | A | 8/1994 | Principato | |
| 5,340,495 | A | 8/1994 | Mulcahy et al. | |
| 5,389,282 | A | 2/1995 | Saijo et al. | |
| 5,407,442 | A | 4/1995 | Karapasha | |
| 5,527,892 | A | 6/1996 | Borsotti et al. | |
| 5,558,659 | A | 9/1996 | Sherrod et al. | |
| 5,595,754 | A | 1/1997 | Ito et al. | |
| 5,607,414 | A | 3/1997 | Richards et al. | |
| 5,607,760 | A | 3/1997 | Roe | |
| 5,649,916 | A | 7/1997 | DiPalma et al. | |
| 5,695,679 | A | 12/1997 | Christie et al. | |
| 5,770,643 | A | 6/1998 | Wehner et al. | |
| 5,807,361 | A | 9/1998 | Kajikawa et al. | |
| 5,899,893 | A | 5/1999 | Dyer et al. | |
| 6,110,158 | A | 8/2000 | Kielpikowski | |
| 6,168,654 | B1 | 1/2001 | Nohr et al. | |
| 6,172,031 | B1 | 1/2001 | Stevens | |
| 6,322,544 | B1 * | 11/2001 | Laughlin et al. | 604/290 |
| 6,436,080 | B1 | 8/2002 | Carlucci et al. | |
| 6,511,465 | B1 | 1/2003 | Freiburger et al. | |
| 6,559,353 | B1 | 5/2003 | Sheridan | |
| 6,663,611 | B2 | 12/2003 | Blaney et al. | |
| 6,669,932 | B2 * | 12/2003 | Imanaka et al. | 424/62 |
| 6,730,819 | B1 | 5/2004 | Pesce | |
| 6,838,423 | B2 | 1/2005 | Irvin et al. | |
| 6,888,044 | B2 | 5/2005 | Fell et al. | |
| D558,335 | S | 12/2007 | Willhaus | |
| 7,504,551 | B2 | 3/2009 | Herfert et al. | |

(Continued)

FOREIGN PATENT DOCUMENTS

| | | |
|---|---|---|
| EP | 0 355 842 A2 | 2/1990 |
| EP | 0 470 275 A1 | 2/1992 |

(Continued)

OTHER PUBLICATIONS

*Field Guide to Stains*, Quirk Publications, Inc., 2002, pp. 199-202.

"Seeing Spots? Don't Rely on Quick Stain Removers," *Consumer Reports*, Aug. 2006, p. 9.

"Stain Removers: Which are Best," Consumer Reports, Mar. 2000, p. 52.

"On-the-Spot Cleanup,", *Consumer Reports*, Jun. 1998, p. 10.

Cost, F., *Pocket Guide to Digital Printing*, Delmar Publishers, Albany, NY, ISBN 0-8273-7592-1, pp. 144-145.

ASTM Designation: E1164-02, "Standard Practice for Obtaining Spectrometric Data for Object-Color Evaluation," Published Aug. 2002.

Japanese Industrial Standard, JIS Z8722-2000, "Methods of colour measurement—Reflecting and transmitting objects," Revised May 20, 2000.

Patent Cooperation Treaty Search Report from the International Search Authority, International Application No. PCT/IB2008/051205 dated Oct. 1, 2009.

*Primary Examiner* — Ali Soroush

(74) *Attorney, Agent, or Firm* — Kimberly-Clark Worldwide, Inc.

(57) ABSTRACT

A composition for a medium that can discharges organic unsaturated colorant molecules that may stain is described. The composition can quickly and effectively neutralize a discoloration that results from, in particular, blood or blood-based, ink, or grease stains. The composition can remove the stain within, typically about 20-30 minutes, and can achieve color contrast of a ΔE value of about 15-20 or greater. The composition can be adapted for different uses and embodied in various cleaning, stain-fighting, cosmetic, personal hygiene, or medical products.

28 Claims, 2 Drawing Sheets

(56) References Cited

U.S. PATENT DOCUMENTS

2002/0054918 A1 5/2002 Murad
2002/0120242 A1 8/2002 Tyrrell et al.
2003/0100877 A1 5/2003 Erdman
2003/0103916 A1* 6/2003 Imanaka et al. ................ 424/62
2003/0119202 A1 6/2003 Kaylor et al.
2003/0162681 A1 8/2003 Hage et al.
2003/0208173 A1 11/2003 Lagerstedt-Eidrup et al.
2004/0060112 A1 4/2004 Fell et al.
2004/0127883 A1 7/2004 Cowell et al.
2005/0079637 A1 4/2005 Wilhelm et al.
2005/0148488 A1 7/2005 Jekel et al.
2005/0163730 A1* 7/2005 Rosevear et al. ............... 424/59
2005/0214241 A1 9/2005 Kandil
2005/0256022 A1 11/2005 May et al.
2006/0111266 A1 5/2006 Abera et al.
2006/0189817 A1* 8/2006 Horlacher et al. ............ 554/126
2006/0198797 A1* 9/2006 Giniger ........................... 424/53
2006/0222675 A1 10/2006 Sabnis et al.
2007/0027049 A1 2/2007 Rigg
2007/0087954 A1 4/2007 Wang et al.
2007/0116748 A1 5/2007 Isele et al.
2007/0122360 A1* 5/2007 Oniki et al. .................... 424/53
2008/0276379 A1 11/2008 MacDonald et al.
2010/0278759 A1* 11/2010 Murad ........................... 424/59

FOREIGN PATENT DOCUMENTS

EP 1 034 804 A1 9/2000
GB 1 349 955 A 4/1974
GB 2 090 137 A 7/1982
GB 2 390 853 A 1/2004
JP 01-186809 A 7/1989
JP 03-172400 A 7/1991
WO WO 97/46219 A1 12/1997
WO WO 99/26588 A2 6/1999
WO WO 00/37039 A1 6/2000
WO WO 01/16268 A1 3/2001
WO WO 03/041752 A1 5/2003
WO WO 2006/062679 A2 6/2006
WO WO 2006/117055 A1 11/2006
WO WO 2011/002949 A1 1/2011

* cited by examiner

COLORANT NEUTRALIZER

FIELD OF INVENTION

The present invention pertains to a material composition and method for decolorizing or neutralizing various organic colorants and stains. The composition and the possible embodiments that may contain it can be used on either a solid article or in a solution-based medium. In particular, the invention describes a composition and reaction mechanism affecting macrocyclic and linear polyunsaturated compounds in colorant systems.

BACKGROUND

Traditionally, blood is regarded as among the most difficult kinds of stain, along with ink and grease, to clean and remove. Removing blood stains, for example, from clothing is an arduous and timely process where care has to be used so as not to set the stain into the fabric permanently. The typical process involves rinsing the fabric with cold salt water (not hot water as this would set the stain into the fabric making it almost impossible to remove). Next, the fabric is soaked in cold water containing an enzyme-based detergent or meat tenderizer for about 30-60 minutes. One would then apply a laundry pre-soak and then launder with enzyme-based detergent. (See e.g., FIELD GUIDE TO STAINS, pp. 199-202, Quirk Publications, Inc. ©2002) This course of treatment can be truly a time consuming process.

Recent stain removers use an oxidant method for removing blood stains, for example, applying an oxidizing agent to the stain-affected area. U.S. Pat. No. 6,730,819 claims the use of oxidizing agents, including oxides, peroxides, ozonides, and superoxides. Most of these agents are irritants or caustic to human skin and therefore not suitable for use in various consumer products, such as feminine hygiene pads or other applications that contact skin. In a series of studies, Consumer Reports, a leading U.S. publication for consumer products, evaluated currently available commercial spot and stain-removers and found that they either do not work effectively against or are not recommended for blood, ink or grease spots or stains. (See, CONSUMER REPORTS, *"Seeing Spots? Don't Rely on Quick Stain Removers*," p. 9, August 2006; CONSUMER REPORTS, *"Stain Removers. Which are Best*," p. 52, March 2000; and CONSUMER REPORTS *"On-the-Spot Cleanup*," p. 10, June 1998.) Some of the commercial spot and stain removers state explicitly on their packaging "not effective on blood, ink and grease."

Currently, given the absence of a viable composition or commercial product, a need exists for a better kind of stain remover, especially one that works well on blood, ink, or grease, among other colorants or stains. Workers in various different industries, such as relating to household or industrial cleaning, laundry, textiles, cosmetics, or health and hygiene, will appreciate a stringent, but less caustic stain removing formulation that can neutralize or discharge various kinds of colorants at a relatively rapid rate. The formulation should be inexpensively derived from natural products and may be applied to articles that can contact naked skin or on a variety of different materials and in a variety of products without harmful effects.

SUMMARY OF THE INVENTION

The present invention in part provides a composition that can be used in a medium for discharging an organic colorant or stain. The composition is a stringent stain-fighter without being chemically harsh. The composition has a formulation that is based on natural ingredients that will not fade or decolor the original colors of a textile or other articles that may be treated with the stain-fighting medium. The composition is non-caustic, having a chemical nature that is gentle enough to permit the colorant neutralizing agent to be applied directly on or near human skin or other body parts. The composition comprises: an aqueous or other polar solvent-based solution (e.g., alcohol) containing about 0.01% to about 95% by volume of an unsaturated aliphatic acid or ester. The aliphatic acid or ester molecule has a carbon chain of at least $C_8$ or greater, and more than one carbon-carbon double bond. One may optionally include a cell-lysing agent in the composition, in which the unsaturated aliphatic acid or ester and cell lysing agent are present in amounts expressed as a ratio ranging from about 1:1 or 1:5 up to about 25:1 or 30:1, respectively. Additionally, the composition may have an oxidizing agent, such as peroxides or cyclic peroxides. The unsaturated fatty acid may include at least one of the following: a) linoleic acid ($C_{18}$:2); b) alpha-linolenic acid ($C_{18}$:3); c) arachidonic acid ($C_{20}$:4); d) eicosapentaenoic acid ($C_{20}$:5); docosahexaenoic acid ($C_{22}$:6); or e) eicosadienoic acid ($C_{20}$:2); f) eicosatrienoic acid ($C_{20}$:3); or g) a combination thereof.

In another aspect, the present invention may be embodied in a variety of commercial cleaning, cosmetic, hygiene, or medical products. For instance, the composition may be incorporated in a stain-remover for use on many kinds of textile fabrics, both woven and nonwoven. Another may be a topical cosmetic product that lessens or discharges the colors of bruises or scars on skin. Yet, another is an oral care or dental whitening product that can remove stains from teeth.

In yet another aspect, the present invention pertains to a method of neutralizing an organic colorant or stain, the method comprises: providing a substrate with an area that is discolored with a substance having at least a molecular structure containing either a macrocyclic or linear hematin or linear unsaturated carbon chains or a cyclic aromatic chromophore; treating the discolored area with a composition or medium containing unsaturated fatty acids or esters thereof, and a surfactant or a cell-lysing agent in amounts expressed as a ratio ranging from about 1:5 up to about 30:1, respectively.

Additional features and advantages of the present invention will be revealed in the following detailed description. Both the foregoing summary and the following detailed description and examples are merely representative of the invention, and are intended to provide an overview for understanding the invention as claimed.

BRIEF DESCRIPTION OF THE FIGURES

FIG. 2A shows a white cotton fabric stained with a hemoglobin solution. FIG. 2B shows the stained fabric immediately after a colorant neutralizer composition (83% linoleic acid, 14% water, 3% Surfynol 465 surfactant) is applied. FIG. 2C shows the stained fabric a few minutes later at an intermediate state, where the color of the stain is decolorizing (i.e., fading), followed by FIG. 2D, where the stain is complete decolorized.

DETAILED DESCRIPTION OF THE INVENTION

Figure 1:
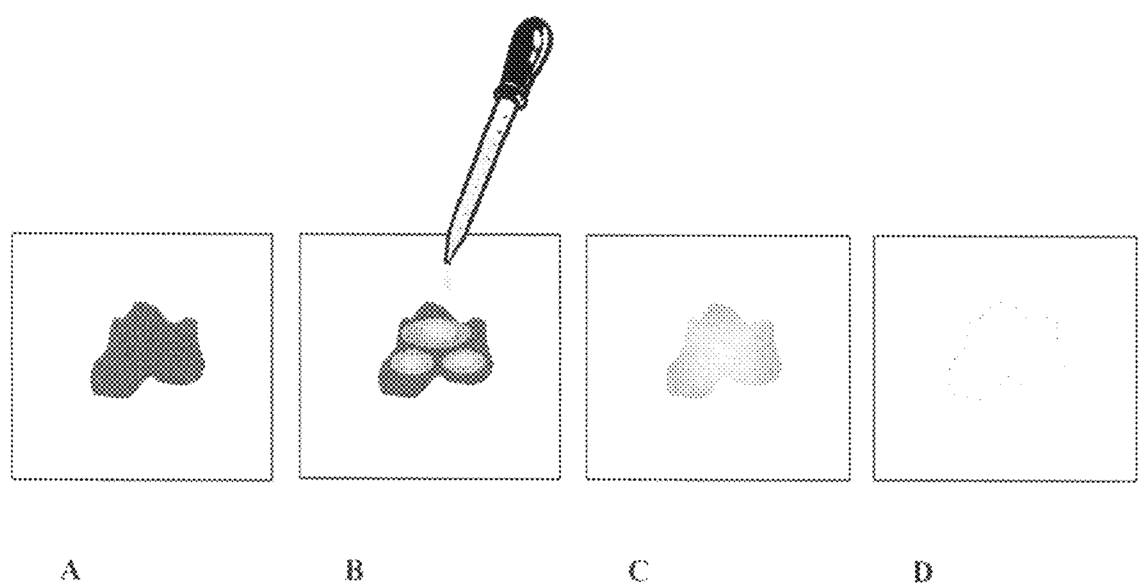
FIG. 1 is a schematic illustration of a stain that is treated with an amount of the present inventive color neutralizing composition. As depicted, from frames A-D, a stain occurs, an amount of active stain remover medium or solution is applied to cover the stain, the stain starts to fade rapidly, and finally becomes undetectable with the naked eye.

The present invention derives in part from the discovery that an unsaturated aliphatic acid or ester can discharge or neutralize efficiently the color of a wide range of macrocyclic and polyunsaturated colored compounds. As used herein, the terms "discharging" or "neutralizing" refers to the ability to change the colored material to a colorless state by a chemical means other than pH reaction or salt formation. In other words, the color is mutated. Although not to be bound by theory, it is believed that the fatty acids are involved in the color discharge mechanism through a free-radical addition reaction that interrupts or breaks the electron cloud of the unsaturated chromophore, and results in a partially saturated colorant molecule. Hence, color mutating involves, in part, the alteration or destruction of a chromophore molecule directly in the stain to yield a colorless product. The present invention, we envisioned, can be used to develop a new efficacious, stain-fighting technical solution to a variety of industries that may need to remove colors, thereby delivering a solution to unmet consumer needs. A product containing the present stain-removing composition can achieve its action by application to the stain without need for subsequent chemical or physical treatment steps.

The composition medium can function at ambient room temperatures and under mild environmental or physical conditions (i.e., close to normal atmospheric pressures and temperatures, and does not involve either pre- or post-treatment with harsh chemical bleaches or oxidants, nor overly vigorous physical agitation).

The ratios of the respective components in the present compositional can be optimized to address various kinds of staining compounds. When optimized for a specific stain, the stain-fighting compositional medium can neutralize a colorant under about 10 minutes, typically within 3 or 5 minutes. For example, once applied to a stain affected area, the active agent can discharge blood stains within about 2 minutes, chlorophyll in within about 3 minutes, and vitamin B12 within about 5 minutes. Blue ink can be discharged in under about 10 minutes. In addition, simpler aromatic cyclic dyes such as indigo carmine and Rose Bengal can be rendered colorless by this fatty acid-based composition.

In another application the fatty acid composition can be safely and effectively used to brighten and clean stains on teeth and other dental fixtures by application of the composition to the oral objects for less than 10 minutes. Still in yet another application the composition was demonstrated to discharge the color of hemoglobin metabolic products, such as, bilirubin (jaundice pigment), stercobilin (brown pigment in feces that gives it its characteristic brown color) and skin pigmentations such as melanin (freckles and age spots) which were all efficiently and fully discharged to yield a colorless product.

The present composition can be embodied in a variety of delivery forms, such as a liquid, a gel, a soft paste, or a solid. For instance, a cellulose or polymer matrix impregnated with at least one kind or a combination of the effective aliphatic acids can be made into a stick or block-type eraser product for easy delivery and use on any stain form. When formulated into a dry solid, such as a dry bar system (based on starch, gelatin, cellulose paste) or soap, water, alcohol, glycerol, or other liquid can be incorporated. A liquid mediated carrier or means of delivery may be preferred since the diffusion of the fatty acid/surfactant can be relatively slow with a dry delivery vehicle. According to another embodiment, one may employ laponite materials (clay-like material) which form a solid phase but have shear-thinning properties. When a force is exerted on the solid, such as rubbing against a surface, the solid material turns to a liquid for easier application to a stained substrate.

In accordance, the present invention also relates to a method of discharging a stain. The method comprises: providing an article that has at least a portion stained with an organic colorant; contacting said stained portion with a medium containing an unsaturated aliphatic acid or ester thereof, said aliphatic acid or ester having a carbon chain with at least C8 and two double bonds; reacting said aliphatic acid or ester with a macrocyclic or linear polyunsaturated colorant molecule. The method may involve heating the medium to increase the reaction kinetics by a factor of two. The unsaturated fatty acids can be applied to a discolored area in either a liquid, semi-solid, or solid phase. The solid phase medium is activated by contacting with water.

I. Theory Of Active Mechanism

According to the present invention, the technology involves the use of an aliphatic acid, such as linoleic acid and linolenic acid, or their chemical analogues, an oxidizing agent, and optionally a cell-lysing agent, such as a surfactant, in an aqueous or polar solvent-based solution or mixture in neutralizing colorants. Although not to be bound by theory, empirical results suggest that unsaturated aliphatic acid molecules with longer carbon chain (at least C8 or longer) lengths and having more than one carbon-carbon double bond (i.e., at least two carbon-carbon double bonds, desirably three or more) contained within the chain are effective to discharge colorants. It may be desirable that the carbon-carbon double bonds are conjugated in the fatty acid molecule. Saturated fatty acids or short chain unsaturated acids (<C8), on the other hand, do not discharge colorants. To be more specific multiple double bonds per chain are preferred, therefore it is believed that the double bonds are involved with the color discharge mechanism.

With regard to the mechanism of reaction, unsaturated fatty acids tend to have a short shelf life and become rancid with time. This rancid nature is due to the fatty acids undergoing auto-oxidation as they react with the oxygen from the air at room temperature. This process involves the oxidative saturation of double bonds and formation of peroxides. Peroxides break down into hydrocarbon byproducts, such as ketones, aldehydes, and small amounts of epoxides and alcohols. Heavy metals present at low levels in fats and oils promote auto-oxidation. This oxidation occurs primarily with unsaturated fats by a free radical-mediated process. Processes that involve free-radical chemistry can generate highly reactive peroxide molecules tend to destroy nutrients in food, cause rancid foods and oils, which are responsible for producing unpleasant and obnoxious odors and flavors. Under certain conditions, rancidity, and the destruction of vitamins, occurs very quickly.

Figure 2:
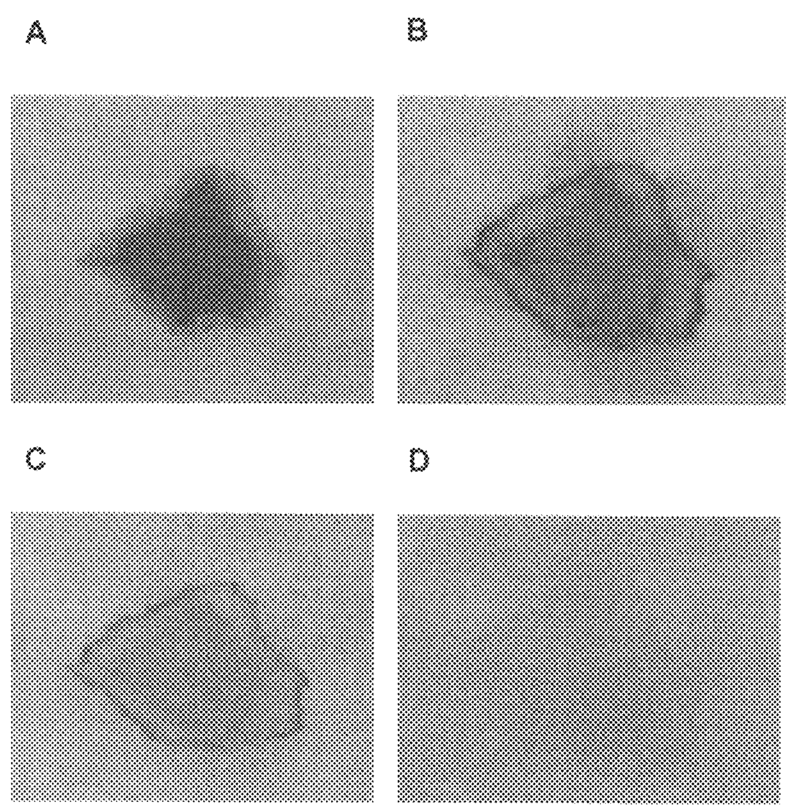
FIG. 2A-D are a series of photographs (grayscale) of an actual stain treated with an effective colorant neutralizer composition according to the present invention.

The accompanying FIGS. 1 and 2, illustrate generally the efficacy of the present composition on another color staining compound. While for purposes of illustration, the linoleic and linolenic acid systems are discussed herein, it is believed that the mechanism is also applicable to other kinds of aliphatic acids and esters. The linoleic system exhibits an oxidizer mechanism with respect to the double bonds of unsaturated carbon chains. Although not to be bound by theory, we theorize that the mechanism of the reaction of the linoleic acid with colorant species involves auto-oxidation of linoleic acid to form peroxides which discharge the color of the stains. We believe that the colorants in the stain catalyze the auto-oxidation of the fatty acids which in turn destroy the colorants. In a test to determine the level of peroxide present in the linoleic acid/surfactant mixture, about 1 ml of an acid potassium iodide mixture in water is added to 25 mg of the linoleic acid/surfynol mixture. After shaking the solution, the color of the solution immediately turns dark brown. Ordinarily, the presence of peroxide turns the solution light yellow by generation of the iodine. Due to the deep brown color (i.e., significant generation of iodine), one can deduce that the linoleic acid mixture has a significant amount of peroxide present. Hence, it is believed that the colorant of the stain promotes oxidation of the fatty acids to form peroxides, which in turn decompose into very reactive alkoxy radical species which rapidly decolorize the colorant by destroying the chromophore. In another example, a blue-colored ink from a ballpoint pen is applied to cotton and paper. Ink is the second toughest kind of stain to remove. The linoleic acid-based composition is applied to the ink spot and fully discharges the color in a relatively short time.

II. Composition

According to the invention, the present stain-fighting composition includes aliphatic acids and/or their esters, and desirably a catalytic amount of an oxidant and/or a cell lysing agent. The composition may have about 0.01% to about 95%, typically about 0.1-70% or 75%, or more typically about 1-50%, by volume of the aliphatic acid or its ester contained in an aqueous or other polar solvent-based solution or medium. The aliphatic acid or ester includes at least one of the following: linoleic acid; alpha-linolenic acid; eicosadienoic acid; eicosatrienoic acid; arachidonic acid (also known as eicosatetraenoic acid); eicosapentaenoic acid; or docosahexaenoic acid. The cell lysing agent can be selected from a surfactant, alcohol, base, self-heating agent, quaternary ammonium compounds, and non-isotonic solutions. In particular embodiments, the surfactant can be: Surfynol 465, Tween 20, Triton X-100, Glucopon 220UP, Ahcovel Base N62 or mixtures thereof. In the composition, the unsaturated aliphatic acid or ester and cell lysing agent are present in amounts expressed as a ratio ranging from about 1:1 up to about 30:1, respectively, desirably to about 15:1 or 25:1, or in amounts expressed as a ratio ranging from about 1:7 up to about 10:1, respectively. To enhance the reaction rate of the aliphatic acid against chromophore molecules, a trace or catalytic amount of an oxidizing agent can be included in the present composition. The oxidizing agent can be present in an amount from about 0.02% or 0.5% to about 1% by volume, desirably from about 0.15 to about 0.75% by volume, and more desirably from about 0.2 to about 0.3 or 0.45% by volume, and may be include, for example, a stabilized peroxide (e.g., urea peroxide). It is believed that an initial amount of oxidizing agent helps to accelerate the rate at which cyclic peroxide is formed. As more peroxide develops, the oxidizer feeds a self-catalyzing reaction, accelerating the reaction rate to discharge colorant stain. The oxidizer breaks down into alkyl radicals that attack colorant molecules.

The composition medium containing unsaturated fatty acids can be applied to a discolored area in either a liquid, semi-solid, or solid phase. The present composition can be used over a wide range of temperatures—from freezing to nearly boiling. For instance, one can use the composition medium at ambient room temperature (~20-27° C.) or may heat the composition to a temperature of about 40-50° C. or even about 80-90° C. and apply the medium to a discoloration. Over such a wide temperature range, one can achieve relatively rapid effect against the stain. Although still effective against a stain, the rate or kinetics of the reaction of the composition medium against the stain tends to slow to about a quarter or a third at cold (under ~1° C.) temperatures than compared to the rate at warmer temperatures.

1. Fatty Acids

According to the invention, the fatty acid molecules that may be incorporated in the composition have a carbon chain of at least C8, desirably greater than C10 or C15, and more than one carbon-carbon double bond (i.e., at least 2, desirably 3 or more). Various aliphatic acids or esters can be employed in the present invention. For instance, an unsaturated fatty acid may include at least one of the following: a) linoleic acid ($CH_3(CH_2)_4CH{=}CHCH_2CH{=}CH(CH_2)_7COOH$ or C18:2); b) alpha-linolenic acid ($CH_3CH_2CH{=}CHCH_2CH{=}CHCH_2CH{=}CH(CH_2)_7COOH$ or C18:3); c) arachidonic acid ($CH_3(CH_2)_4CH{=}CHCH_2CH{=}CHCH_2CH{=}CHCH_2CH{=}CH(CH_2)_3COOH$ or C20:4); d) eicosapentaenoic acid ($CH_3(CH_2CH{=}CH)_5(CH_2)_3COOH$ or C20:5); docosahexaenoic acid ($CH_3(CH_2CH{=}CH)_6CH_2CH_2COOH$ or C22:6); or e) eicosadienoinc acid, f) eicosatrienoic acid ($CH_3(CH_2)_3(CH_2CH{=}CH)_3(CH_2)_6COOH$ or C20:3); or g) a combination thereof. Table 1 lists different kinds of fatty acids as arranged in three groups: A) omega 6, B) omega 3, or C) omega 9. According to the invention, the omega 3 and 6 fatty acids function better as stain-fighters than omega 9 fatty acids because the first groups contain greater numbers of unsaturated bonds.

TABLE 1

| Common name | Lipid name | Chemical name |
|---|---|---|
| A. List of omega-6 fatty acids | | |
| Linoleic acid | 18:2 (n-6) | 9,12-octadecadienoic acid |
| Gamma-linolenic acid | 18:3 (n-6) | 6,9,12-octadecatrienoic acid |
| Eicosadienoic acid | 20:2 (n-6) | 11,14-eicosadienoic acid |
| Dihomo-gamma-linolenic acid | 20:3 (n-6) | 8,11,14-eicosatrienoic acid |
| Arachidonic acid | 20:4 (n-6) | 5,8,11,14-eicosatetraenoic acid |
| Docosadienoic acid | 22:2 (n-6) | 13,16-docosadienoic acid |
| Adrenic acid | 22:4 (n-6) | 7,10,13,16-docosatetraenoic acid |
| Docosapentaenoic acid | 22:5 (n-6) | 4,7,10,13,16-docosapentaenoic acid]] |
| Calendic acid | 18:3 (n-6) | 8E,10E,12Z-octadecatrienoic acid |
| B. List of omega-3 fatty acids | | |
| α-Linolenic acid (ALA) | 18:3 (n-3) | octadeca-9,12,15-trienoic acid |
| Stearidonic acid | 18:4 (n-3) | octadeca-6,9,12,15-tetraenoic acid |
| Eicosatetraenoic acid | 20:4 (n-3) | eicosa-8,11,14,17-tetraenoic acid |
| Eicosapentaenoic acid (EPA) | 20:5 (n-3) | eicosa-5,8,11,14,17-pentaenoic acid |
| Docosapentaenoic acid | 22:5 (n-3) | docosa-7,10,13,16,19-pentaenoic acid |
| Docosahexaenoic acid (DHA) | 22:6 (n-3) | docosa-4,7,10,13,16,19-hexaenoic acid |
| C. List of omega-9 fatty acids | | |
| oleic acid | 18:1 (n-9) | 9-octadecenoic acid |
| eicosenoic acid | 20:1 (n-9) | 11-eicosenoic acid |
| mead acid | 20:3 (n-9) | 5,8,11-eicosatrienoic acid |
| erucic acid | 22:1 (n-9) | 13-docosenoic acid |
| nervonic acid | 24:1 (n-9) | 15-tetracosenoic acid |

2. Natural Oil Containing Fatty Acid Esters

Many of these unsaturated aliphatic acids are present as a glyceride component of natural-occurring seed oils, such as safflower, grape or pumpkin or soybean, or linseed, or peanut, or poppy, or perilla or a mixture thereof. These fatty acids can be easily and inexpensively extracted from these common seeds. For example, linoleic acid is stored usually in the form of glycerol and found in the seeds of certain plants, such as grapes, flax, safflowers, and peanuts, and fish. The highest levels of linoleic acid are in safflower (carthame) seeds (68-80%), grape seeds (65-73%), and pumpkin seed oil (45-60%). When hydrolyzed into an acid form, it is believed that the active agent in the linoleic acid attacks the conjugated unsaturated bonds in the structure of the colorant molecule.

While pure linoleic and linolenic acids can be used to discharge the stain color, the natural seed oils containing esters of these acids can also be used. Table 2, provides a list of some examples of natural seed oils and their linoleic and linolenic acid content, respectively.

TABLE 2

| Seed | Linolenic Acid % total oil | Linoleic Acid % total oil |
|---|---|---|
| Almond | 0 | 17 |
| Avocado | 0 | 10 |
| Beech | 0 | 32 |
| Brazil | 0 | 24 |
| Cashew | 0 | 6 |
| Chia | 30 | 40 |
| Coconut | 0 | 3 |
| Corn | 0 | 59 |
| Cotton | 0 | 50 |
| Evening Primrose | 0 | 81 |
| Filbert | 0 | 16 |
| Flax | 58 | 14 |
| Grape | 0 | 71 |
| Hemp | 20 | 60 |
| Hickory | 0 | 17 |
| Candlenut | 29 | 40 |
| Macadamia | 0 | 10 |
| Neem | 1 | 20 |
| Olive | 0 | 8 |
| Palm kernel | 0 | 2 |
| Peanut | 0 | 29 |
| Pistachio | 0 | 19 |
| Pumpkin | 8 | 50 |
| Rice bran | 1 | 35 |
| Safflower | 3 | 75 |
| Sesame | 0 | 45 |
| Soybean | 7 | 50 |
| Sunflower | 0 | 65 |
| Walnut | 6 | 51 |
| Wheatgerm | 5 | 50 |

3. Cell-Lysing Agents: Surfactants

Various kinds of surfactants, either individually or in combinations thereof, may be incorporated into certain embodiments of the present invention. Table 3 lists examples of classes and types of surfactants that are suitable.

TABLE 3

| ANIONIC SURFACTANTS |
|---|
| Alkyl Ether Phosphates |
| Alkyl Ether Carboxylic Acids and Salts |
| Alkyl Ether Sulphates |
| Alkyl Naphthalene Sulphonates |
| Alkyl Phosphates |
| Alkyl Benzene Sulphonic Acids and Salts |
| Alkyl Phenol Ether Phosphates |
| Alkyl Phenol Ether Sulphates |
| Alpha Olefin Sulphonates |
| Aromatic Hydrocarbon Sulphonic Acids, Salts and Blends |
| Condensed Naphthalene Sulphonates |
| Di-alkyl Sulphosuccinates |
| Fatty Alcohol Sulphates |
| Mono-alkyl Sulphosuccinates |
| Alkyl Sulphosuccinamates |
| Naphthalene Sulphonates |
| AMPHOTERIC SURFACTANTS |
| Alkyl Ampho(di)acetates |
| Amido Betaines |
| Alkyl Betaines |
| CATIONIC SURFACTANTS |
| Alkyl Dimethylamines |
| Alkyl Amidopropylamines |
| Alkyl Imidazoline Derivatives |
| Quaternised Amine Ethoxylates |
| Quaternary Ammonium Compounds |
| NONIONIC SURFACTANTS |
| Alkyl Polysaccharides |
| Amine Oxides |
| Block Copolymers |
| Castor Oil Ethoxylates |
| Ceto-Oleyl Alcohol Ethoxylates |
| Ceto-Stearyl Alcohol Ethoxylates |
| Decyl Alcohol Ethoxylates |
| Dinonyl Phenol Ethoxylates |
| Dodecyl Phenol Ethoxylates |
| End-Capped Ethoxylates |
| Ether Amine Derivatives |
| Ethoxylated Alkanolamides |
| Ethylene Glycol Esters |
| Fatty Acid Alkanolamides |
| Fatty Alcohol Alkoxylates |
| Lauryl Alcohol Ethoxylates |
| Mono-branched Alcohol Ethoxylates |
| Natural Alcohol Ethoxylates |
| Nonyl Phenol Ethoxylates |
| Octyl Phenol Ethoxylates |
| Oleyl Amine Ethoxylates |
| Random Copolymer Alkoxylates |
| Sorbitan Ester Ethoxylates |
| Stearic Acid Ethoxylates |
| Stearyl Amine Ethoxylates |
| Synthetic Alcohol Ethoxylates |
| Tall Oil Fatty Acid Ethoxylates |
| Tallow Amine Ethoxylates |
| Trid Tridecanol Ethoxylates |
| POLYMERIC SURFACTANTS |
| MethoxyEG Methacrylate Comb-Graft Copolymer |
| Polycarboxylates |

III. Ratio And Rate

The inventive technology has proven to be efficacious in removing the color from substrates that have been treated with either a macrocyclic and/or linear polyunsaturated colored compounds. According to the invention, a colorant or stain that is treated with the present composition can be discharged or neutralized within a period of about 60 minutes or less. Typically, depending on the concentration, the color will be eliminated within well under 20 or 30 minutes. According to certain examples the color is discharged within about 15 minutes, or for faster action within about 3 minutes after application of the composition to a stain. One can observe that the color of the discoloration or stain is reduced by 5. In certain other embodiments, the observable color of the stain is reduced by at least a ΔE value of 15 or 20, which lightens the stain to being virtually imperceptible by the naked eye. Typically, the discoloration or stain can be reduced by a ΔE value of about 25-40, desirably up to about 50 to 70 or 80. As will be described in further detail, ΔE is the measurement of color change as defined by 3D color space measurements.

Using a set of blood-stained cotton fabric, we tested the effect of the ratio of linoleic acid and surfynol on the time to discharge. Table 4, summarizes the results, which suggests that even though the various concentrations of the composition were all effective, in certain embodiments to be relatively quick acting, an aliphatic acid to surfactant concentration of about at least 2:1 is desired to discharge the color of various organic colorants and stains.

TABLE 4

Ratio of Linoleic Acid to Surfactant on Time to Discharge Color

| Ratio of Linoleic Acid:Surfactant (Surfynol as a 20% solution) | Time to decolorize fresh blood stain: |
|---|---|
| 5:1 | Approximately 3 minutes |
| 2:1 | 20-60 minutes |
| 1:1 | 4 hours |
| 1:5 | 12 hours |
| 5:1 with 0.3% urea peroxide | 34 seconds |
| 5:1 with 0.1% urea peroxide | 50 seconds |
| 5:1 with 1% urea peroxide | 15 seconds |

Color Measurement

In measuring color, a person certainly can evaluate the relative shades and hues of color by means of comparison using the naked eye. For an objective standard, however, a method of evaluation that provides the observer with numerical data along with a process to quantify that data is needed using a spectrophotometer, and a color interpretation method: Delta-E (ΔE). Color intensity and change may be measured using a conventional test known as "CIELAB", which is discussed in *Pocket Guide to Digital Printing* by F. Cost, Delmar Publishers, Albany, N.Y. ISBN 0-8273-7592-1, at pages 144 and 145, the contents of which are incorporated herein by reference. This method defines three variables, L*, a*, and b*, which correspond to three characteristics of a perceived color based on the opponent theory of color perception. The three variables have the following meaning:

L*=Lightness (or luminosity), ranging from 0 to 100, where 0=dark and 100=light;

a*=Red/green axis, ranging approximately from −100 to 100; positive values are reddish and negative values are greenish; and b*=Yellow/blue axis, ranging approximately from −100 to 100; positive values are yellowish and negative values are bluish.

Because CIELAB color space is somewhat visually uniform, a single number may be calculated that represents the difference between two colors as perceived by a human. This difference is termed ΔE and calculated by taking the square root of the sum of the squares of the three differences (ΔL*, Δa*, and Δb*) between the two colors.

In CIELAB color space, each ΔE unit is approximately equal to a "just noticeable" difference between two colors. CIELAB is therefore a good measure for an objective device-independent color specification system that may be used as a reference color space for the purpose of color management and expression of changes in color. Using this test, color intensities (L*, a*, and b*) may thus be measured using, for instance, a handheld spectrophotometer from Minolta Co. Ltd. of Osaka, Japan (Model # CM2600d). This instrument utilizes the D/8 geometry conforming to CIE No. 15, ISO 7724/1, ASTME1164 and JIS Z8722-1982 (diffused illumination/8-degree viewing system. The D65 light reflected by the specimen surface at an angle of 8 degrees to the normal of the surface is received by the specimen-measuring optical system. Still other suitable devices for measuring the intensity of a visual color may also be used in the present invention. For example, a suitable reflectance reader is described in U.S. Patent App. Pub. No. 2003/0119202 to Kaylor, et al., the content of which is incorporated herein in by reference.

IV. Effect Of Temperature On Rate Of Stain Erasing

To examine the effect of temperature on the relative rate of color discharge for hemoglobin stains on cotton fabric, a series of 6 cm×6 cm square samples of untreated cotton fabric were prepared. Onto each sample was placed 50 μL of a 4% wt./wt. hemoglobin solution in water and allowed to soak into the fabric creating a reddish brown stain. Onto the stain was placed either 100 μL of water (control) or a linoleic acid/surfynol 465 mixture (treated) and briefly rubbed with the aide of a glass rod tip. One set, both control and treated samples, was placed into an oven at 80° C., a second set was placed in an incubator at about 37° C., a third set in a freezer at −5° C., and a fourth set was left at ambient temperature (~22° C.). A worker checked each of the sample sets after about 2 minutes and measured the relative amount of stain discharge. The stain color in each of the sample sets was observed to have almost disappeared with the exception of the sample set in the freezer, which exhibited only a slight decreased in stain color. Except for the sample in the freezer, after about three minutes the stains on the other samples all were erased to leave a colorless moist circle where the stain spot had been. The stain color of the sample in the freezer was observed to have lessened only by half of its original color intensity. The freezer sample was still effective under 30 minutes, but took up to a full 20 minutes in order to fully discharge the stain color. From these results, it appears that ambient or elevated temperatures do not significantly affect the stain erasing mechanism kinetics. Temperatures below freezing, however, can slow down the stain erasing kinetics and therefore increase the overall time to discharge a colorant.

VI. Embodiments & Products

According to certain embodiments, we envision that various applications can be derived from the present technology. For instance, a major class of products or product concepts may include stain or colorant dischargers that erase or neutralize, for example, the color of blood on clothing textiles and other materials.

The composition can be embodied and/or delivered in a variety of the forms, such as an aerosol, a liquid, a gel, a paste, or a solid. When in a gel or solid form, the delivery media can be either shear thinning or temperature responsive, which becomes a liquid during application. A solid phase medium can also be activated by contacting said with water. The composition can be used on surfaces of fabrics, clothing, skin, fur, carpet, walls, enamel, glass, metal, or agar and growth media.

In another embodiment, we contemplate that the composition be used in a stain-fighting product. The stain-fighting product can comprise an aqueous or polar-solvent based solution of polyunsaturated fatty acids and a cell-lysing agent in amounts expressed as a ratio ranging from about 1:1 or 1:5, up to about 30:1, respectively. More typically, the fatty acids and cell lysing agent are present in amounts expressed as a ratio ranging from about 1:7 up to about 25:1, respectively. For certain embodiments, favored ratios are about 15:1 or 20:1, respectively. When using a surfactant, the surfactant can be present in about 1-10-20% concentration or about 5-20%, desirably about 5% to 15%, by volume of polyunsaturated aliphatic acid or ester. The fatty acids are present as esters of alkyl alcohols, cyclic aliphatic alcohols, aromatic alcohols, glycerides, glycols (diols), polyvinyl alcohols, or polyethers. An oxidizing agent, which may be either peroxide or cyclic peroxide, also can be included and present in an amount from about 0.05% to about 1% by volume. Desirably, the amount of oxidizing agent is present in an amount from about 0.15-0.55-0.75% by volume.

1. Blood and Menses-Stain Remover

From empirical tests, we have discovered that the composition is highly effective to discharge the color of blood or menses. Hence, it can be a good aesthetic agent for use in bandages, medical patches, wraps, personal absorbent articles, medical drapes, meat trays and pads, and inner or outer garments because it discharges the stains and reduces the fear of the stain. For example it could be in a bandage which discharges the color of blood or applied around the catheter puncture area so as to discharge the small amounts of dried blood which typically builds up around the puncture wound.

In another example, one may enable feminine care product manufacturers or cleaners to design a specific product to erase the red or reddish-brown color of menses or blood stains. One embodiment may be to incorporate a built-in release pack or other vessel for the present composition medium to discharge the color when activated in feminine pads. The vessel may be situated along the periphery to prevent leaks from spreading out beyond the edge of the pad. Alternatively, the vessel may affect the whole absorbent section of the pad except for a small portion that serves as a visual indicator for the user.

According to Consumer Reports, blood, ink, and grease are three of the most difficult staining agents to remove. The difficulty to remove or erase a stain can be aggravated even more when one is traveling or away from home with no access to detergents or laundering facilities.

Some common consumer cleaning or bleaching products currently available commercially, such as the TIDE®-to-go pen by Proctor and Gamble (e.g., U.S. Pat. No. 6,838,423) that uses a peroxide, SHOUT®-stain remover by SC Johnson Brands that uses surfactants, and Clorox products that incorporates a hypochlorite bleach as the active agent, state on their packaging that the product does not work well on blood, ink or grease stains.

The difficulty with blood stains is due in part to the nature of the hemoglobin molecule in blood, which undergoes a color change from red to brown, black or green when the molecule is oxidized, reduced, or the iron is removed from it. Improper application of some of these products against difficult stains have actually fixed (i.e., made permanent), instead of removing the stains.

Since so few products can achieve the difficult challenge of neutralizing such stains, we believe that an advantage and unique feature of the present invention is that one can have a product that actually removes blood, as well as ink, stains with an initial one-step application of the composition medium, without the need for either additional pre- or post-treatments with other cleaning agents.

2. Potential use for Skin Pigmentation Lightening or Color Discharge

An advantage of the present chemistry is that it is suitably mild for use on skin contact approved articles and works at ambient temperatures and conditions. The present compositions may also be incorporated into certain cosmetic or dermatological products for topical use to reduce the appearance of or fade skin discolorations and unwanted pigmentations, which may result, for example, from bruises, scars, freckles, moles, age (liver) spots, or rose rashes. For instance, normally, when one is bruised it may take several of weeks' time for a subcutaneous blood clot to lighten and dissipate completely. As has already been demonstrated, the fatty acid or ester works well against blood discoloration bruises since the fatty acid can oxidize the hemoglobin molecule. Incorporation of a colorant neutralizer according to the present invention can lighten the bruise and quicken its eventual dissociation. The present composition can be effective against melanin; an over concentration of which may result in freckles, moles, or age spots. According to one embodiment, linoleic acid (62% absorbancy) can be absorbed through the skin to counteract unwanted pigmentation. The cosmetic or dermatological product could be in the form of a cream or elusion, or it may be incorporated as an additive to a plaster or bandage to help squeamish patients to overcome psychologically the sight of blood and feel better.

3. Application to Teeth Cleaning and Whitening/Brightening

An oral care product that can remove tannin stains and whiten teeth is also contemplated. Stains on teeth are typically due to the tannins in dark colored beverages such as tea, coffee and carbonated caramel-colored soft drinks. Plaque is a build up of protein-based materials which can lead to enamel breakdown and cavities. The current commercial products use peroxide based actives such as hydrogen peroxide and/or benzoyl peroxides to bleach the teeth. These actives are strong oxidizers and are documented to etch the surface of the enamel and are also strongly irritating to the gums and tissues of the mouth. The present inventive system provides a natural gentler, hence, safer tooth whitening agent. Tannins that include cyclic chromophores can be oxidized by the fatty acid or ester. This system to discharge the color of stains on teeth was successfully demonstrated in the accompanying Example 16, below. Four extracted wisdom teeth that had stains, plaque, and dried blood were used in a study. Two of the teeth were selected at random and treated with a natural, edible fatty acid. The teeth were placed in 5 ml of a linoleic acid—surfynol 465 mixture (5:1 ratio where the surfactant was a 20% wt/wt solution in water) for about 5 minutes or less (e.g., about 3 minutes) and then removed and rinsed under running water. The teeth were then placed along side the control teeth and visually examined. A dramatic difference is observable when compared with the two teeth in the control sample. The teeth that are treated are significantly whiter and brighter. The dried blood, stains and plaque were discharged to leave spotless teeth. No trace of these colored contaminants could be seen on the teeth even on close inspection. This is a remarkable observation considering that the teeth were only in the solution for a mere 3 minutes.

This active whitening system could be used in a solution form as a liquid rinse, on strips, finger brush applicators or toothbrush or cotton tip. The active agent could be incorporated into toothpaste directly or mouthwash where a user would be instructed to brush or hold in mouth for approximately three minutes duration before a cleaning rinsing. Further, all of these kinds of application methods could apply to the care of dentures or artificial teeth, and by extension to pet and other animal dental-care. It should also be noted that this brightening occurred in minutes and by contrast the commercial products describe the treatment takes days or weeks of regular daily application of a liquid or film strip.

VII. Examples Of Color Neutralization For A Variety Of Colorant Types

The following section shows some empirical results that provide insights to the mechanism by which colorant stains are discharged. These examples offer a glimpse to help to delineate a possible range of colorants against which the present compositions are effective. Table 5 summarizes the observed effect of the present compositions when treating a stained substrate that has been stained with various classes of colorant compounds.

TABLE 5

| Colorant Type | | |
|---|---|---|
| Colorant Class | Compound | Color Discharged |
| Macrocyclics | | |
| Porphyrins | Hemoglobin | Yes |
| | Vitamin B12 | Yes |
| Corrins | Chlorophyll | Yes |
| Porphines | FePFPP | Yes |
| | PFPP | Yes |
| | CuTPPS4 | No |
| | TPPS4 | No |
| Linear polyunsaturated | Carotene | Yes |
| | Bilirubin | Yes |
| Dyes/Colorants | | |
| Xanthene | Rose Bengal | Yes |
| | Indigo carmine | Yes |
| | Ballpoint ink (blue) | Yes |
| | Ballpoint ink (red) | No (reduced in color) |
| Natural Stains | Coffee | Yes |
| | Red wine | No (reduced but not gone) |
| | Mustard | Yes |

TABLE 6

| Surfactant | | |
|---|---|---|
| Surfactant Class | Name | Blood Color Discharged |
| Acetylenic diol | Surfynol 465 | Yes |
| Polyoxyethylene sorbitol | Tween 20 | Yes |
| Tetramethylbutylphenyl polyether | Triton X-100 | Yes |

The presence of a surfactant appears not to influence significantly the color discharge mechanism, as shown by a hemoglobin experiment in which linoleic acid discharges the color of hemoglobin in blood even in the absence of a surfactant. The surfactant, however, lyses the blood cells to facilitate access of the linoleic acid to the macrocyclic hemoglobin molecule.

TABLE 7

| Alkyl Acid Type | | |
|---|---|---|
| Acid | Structure (# of Carbons:# of Double bonds) | Color Discharged |
| Linoleic acid | C18-2 | Yes |
| Linolenic acid | C18-3 | Yes |
| Stearic acid | C18:0 | No |
| Hexanoic acid | C6:0 | No |
| Undecanoic acid | C11:0 | No |
| Octanoic acid | C8:0 | No |
| 2-Butenoic acid | C4:1 | No |
| Acetic acid | C2:0 | No |
| Oleic acid | C18:1 | No |

TABLE 8

| Natural Oils | |
|---|---|
| Name | Blood Color Discharged |
| Safflower | Yes |
| Grape seed | Yes |
| Pumpkin seed | Yes |
| Canola | No |
| Olive | No |

From Table 7, one can see that only natural oils that contain linoleic or linolenic or mixtures undergo a color discharge mechanism. Table 8 records the fact that the activity is not due to the effect or involvement of the carboxylic acid functionality, since all these oils are in the form of glycerol esters, with no free acid group present.

VIII. Empirical Examples

Materials and Details

We conducted a series of experiments as proof of concepts for the present invention. In the experiments a number of different materials were used. Samples of linoleic acid and linolenic acid were purchased from Sigma Chemical Company (St. Louis Miss.), and used without further purification. Surfynol 465 was obtained from Air Products (Allentown Pa.), and Tween 20 was obtained from Aldrich Chemical Company, (Milwaukee Wis.). "TIDE®-to-go" (Proctor and Gamble Cincinnati, Ohio) containing peroxide and surfactant, "SHOUT® wipes" (SC Johnson & Son, Inc., Racine Wis.), and "Clorox bleach pen" (The Clorox Company, Oakland Calif.) containing hypochlorite and surfactants were all commercially available. Cotton batting and (no resin finish) fabric, blue denim (old clean jeans) fabric, satin, polyester and lycra fabrics were used in this study as pre-cut 3"×4" samples. Safflower seed oil (Rapunzel Pure Organics, Valatie N.Y.) and grape seed oil (Liberty Richter, Saddle Brook N.J.) were purchased as cold pressed cooking oils. Vitamin B12 was obtained in liquid form (Now Foods, Bloomingdale Ill.), along with fresh parsley, pumpkin seed oil in the form of gel caplets, and beta-carotene as 25,000 IU softgel capsules (Solgar Vitamin and Herb, Leonia, N.J.). The following colorant compounds were purchased from Aldrich Chemical Company, Milwaukee Wis. and used without further purification: Iron 5,10,15,20-Tetrakis(pentafluorophenyl)-21H,23H-phenylporphine ($FeTPF_5P$); Hemoglobin; Bilirubin mixed isomers (Sigma Chemical Co. St. Louis Mo.); 5,10,15,20-Tetraphenyl-21H,23H-porphine-o,o",o",o'"-tetrasulfonic acid, tetrasodium salt ($TPPS_4$); Stearic acid. Copper 5,10,15,20-Tetraphenyl-21H,23H-porphine-o,o",o",o'"-tetrasulfonic acid, tetrasodium salt ($CuTPPS_4$) (See "Colorant Stabilizers," R. S. Nohr and J. G. MacDonald, U.S. Pat. No. 6,168,654, for synthesis).

1. Blood

The application of linoleic acid combined with a surfactant coated onto the surface of a feminine pad discharged blood color leaving only a trace of pale yellow. This decolorization was achieved at both ambient room and body temperatures and under neutral pH. The following section describes the experiments conducted.

EXAMPLE 1

Blood on Glass Slides

Microscope slides were coated with a mixture of linoleic acid, surfynol 465 and water (ratio 1:0.01:1) and spread out by the use of a glass rod. A drop of blood (human) was placed onto each slide and spread out with the glass rod. The control slide was prepared by simply spreading out the drop of blood. The slides were placed in an incubator at 37° C. for one hour. The blood color was fully discharged on the experimental slides while no change in color was observed with the control slides.

EXAMPLE 2

Blood on Feminine Pads

Four feminine pads were used in a study. Control 1 (C1) just had two drops of human blood placed on the center of the pad. Control 2 (C2) had a light coating of surfynol 465 in water (0.25 ml in 0.5 ml water) placed on the center of the pad followed by two drops of human blood. Experimental pad 1 (E1) had a mixture of linoleic acid and surfactant (0.25 ml surfactant and 0.50 ml of linoleic acid) followed by two drops of human blood. Experimental pad 2 (E2) had a mixture of linoleic acid and surfactant (0.50 ml of surfactant and 0.50 ml of linoleic acid) applied to the center of the pad followed by two drops of human blood. The pads were placed in an incubator at 37° C. and observed. Within minutes the red color of the blood on pads E1 and E2 had turned brown and continued to fade with time. At the end of the experiment the blood color on pads E1 and E2 had been fully discharged, leaving only a pale yellow tint. The blood color on the control pads remained essentially unchanged.

The blood color on pad C2 was visibly lighter as compared to the color on the C1 pad. This suggests that the surfactant itself has a slight effect on the color and this is thought to results from the ability of the surfactant to lyse the blood cells allowing the hemoglobin to be slightly oxidized by the air.

2. Blood and Menses on Textile Fabrics and Pads

EXAMPLE 3

Blood and Menses Stain on Textile Fabrics

Using 4"×5" sample of cotton, satin, polyester and light-weight Lycra were used in a study where blood (20 μl) or menses (50 μl) was placed onto the center of the fabric samples to mimic a stain situation. To determine potential efficacy of stain removal, 200 μl of a control solution (Surfynol 465 surfactant as a 2% wt/wt solution in water) or 200 μl of surfactant solution containing linoleic acid as the stain removal active (1:2 ratio of 2% surfactant solution to linoleic acid) were applied to the area soiled by blood or menses. The samples were then placed in an incubator at 37° C. and the color change visually monitored. It is clear that the intense menses color has abated using the identified technology, offering a significant improvement in the appearance of the fabrics.

EXAMPLE 4

Discharge of Menses Color on Pads

In a number of experiments, feminine pads (Kotex® by Kimberly-Clark Corporation) are pretreated with 200 μl of Surfynol or Tween 20 surfactant in water solution (2% wt./wt.) for use as control samples. Other pads were treated with 200 μl of a mixture of linoleic acid and surfactant (2:1 ratio). All the pads were then insulted with 50 μl of menses.

The pads clearly show that on the control pads, where the menses has wicked to cover a larger patch on the pad, the pad retains the red color. In contrast, the menses on the pad containing the linoleic acid remains fixed in a tight spot and the color has been reduced to a pale yellow.

3. Comparison with Commercial Spot and Stain Removers

EXAMPLE 5

In this section a series of experiments were conducted to compare the ability of the linoleic acid-based system to commercial spot and stain removers to decolorize blood and menses on textiles.

The fabric samples were placed on an aluminum foil sheet. On the center of each sample was placed either 50 μl of menses or 20 μl of blood. Then 200 μl of either Tide®-to-Go, 2 wt % aqueous surfynol (surfactant) solution, linoleic acid in surfynol solution, Shout® wipe fluid or Clorox® bleach pen fluid was pipetted onto the sample stain. The spot was gently mixed with the end of a glass rod for 5 seconds. The samples were then placed in an incubator at 37° C. and visually observed.

Although both the Tide®-to-go and Shout® stain color were slightly reduced, it was due to dilution rather than discharge of the color. The linoleic acid/surfactant system performed the best completely discharging the color of the menses. The Clorox® bleach pen system turned the menses into a black deposit and also bleached the denim.

The same results were also found with the blood stain samples. The linoleic acid system performed the best by complete decolorization of the blood spot. The Clorox® bleach pen turned the blood into a black spot coated with a white deposit (surfactant?). When the sample was turned over, the underside of the fabric had a black spot.

Some of the spot and stain remover products mention on their packaging or web-sites that the product does not work well in removing blood, grease or oil stains. For instance, the website for Tide®-to-Go states:

"Tide®-to-Go does not work as well on greasy stains or on non-food and drink stains including ink, blood, and grass stains. It is OK to try Tide®-to-Go on these stains, but generally they are the type of stains that you should pre-treat and launder with Tide."

4. Preliminary Work with Pumpkin, Safflower and Grape Seed Oils

EXAMPLE 6

As mentioned earlier, linoleic acid is found in a wide variety of seed and fish oils. The oils containing the highest concentration of linoleic acid are safflower (carthame) seed (68-80%), grape seed (65-73%), and pumpkin seed oil (45-60%). A quick experiment was conducted using a sample of pumpkin seed oil applied to pads. In the study, a feminine pad (e.g., Kotex®) had 300 μl of the pumpkin seed oil placed on it. A second pad had 300 μl of a mixture of pumpkin seed oil and surfynol surfactant (ratio 4:1) placed on it. A third pad had 300 μl of the linoleic acid/surfactant mixture used earlier. A forth pad (control) had 300 μl of water placed on it. The pads were then insulted with 20 μl of human blood.

The preliminary results show that the pumpkin seed oil/surfactant mixture discharged the blood color to almost the same extent as the linoleic acid/surfactant mixture. Although the concentration of linoleic acid in this seed oil product is not known, it was clearly a sufficient amount to reduce blood color. The pumpkin seed oil alone (without surfactant) was not sufficient to affect the color. This study demonstrates that natural oils could be used in the pads, which offer the potential for “natural” product labeling, as well as possible skin health benefit claims.

Other oils were also tested on cotton fabric to determine the potential efficacy with blood stains. Safflower and grape seed oils also discharge the red color of blood and significantly reduced the stain color. Neither worked as well as the linoleic acid/surfactant systems in totally discharging the stain.

The activity of these natural products could be improved by reformulation and evaluation of the ratio of oil and surfactant. Linoleic (two double-bonds) and linolenic (three double-bonds) acids worked well with no real differences observed between their activities in discharging the blood color. Linoleic acid is significantly cheaper than linolenic acid. The choice of which form of linoleic acid to use in the product will be determined based upon considerations of safety, cost, and sourcing.

5. Dried Blood on Cotton Fabric

EXAMPLE 7

The question of whether the linoleic acid system would be able to discharge the color of dried blood stains was explored. Fresh human blood was placed onto the center of cotton squares (3"×4") and allowed to completely dry by leaving it for 3 hours. The dried stains were blotted with a paper towel to check that they were indeed dried. No blood was observed on the blotting towel and the stain was therefore determined to be completely dry. Onto one stain were placed two drops of the linoleic acid:surfynol mixture (2:1) and spread over the stain using a glass rod. The samples were then placed in an incubator at 37° C. and the color was observed. The stain color was discharged, however it did take twice as long when compared to a fresh blood stain.

6. Decolorization of Other Colored Compounds by Linoleic Acid

To explore the ability of linoleic acid to decolorize other compounds, molecules were identified that have intense color and which comprise porphyrin macrocycles similar to the hemoglobin in blood. A series of porphyrin-based chemicals were obtained and exposed to linoleic acid, including: pure hemoglobin, chlorophyll, vitamin B12, copper tetraphenylporphine tetrasulfonic acid ($CuTPPS_4$) and corresponding porphines without copper, tetraphenyl-porphine tetrasulfonic acid ($TPPS_4$) and tetraphenylpentafluoroporphine (TPFP).

EXAMPLE 8

Pure Hemoglobin

About 20 mg of pure bovine hemoglobin was dissolved into 1 ml of de-ionized (DI) water. Two drops were placed onto a 3"×4" square of cotton fabric and the same repeated for the control fabric. Two drops of linoleic acid were then placed onto one of the cotton squares having the hemoglobin “stain.” The fabrics were then placed in an incubation chamber (37° C. and 50% humidity). As shown in the accompanying photographs of FIGS. 2A-D, the hemoglobin color was discharged within minutes to give a colorless area where the red stain had been. The red color of the hemoglobin was effectively discharged by the linoleic acid. This illustrates that the surfactant is only required in the case of blood to lyse the blood cell membrane in order to allow the linoleic acid to react with the hemoglobin.

EXAMPLE 9

Chlorophyll

The green colorant in plants, chlorophyll, has a macrocyclic ring similar in base structure to hemoglobin. In contrast to hemoglobin which has iron in the center of the ring, chlorophyll has magnesium in the center. This experiment would determine the role of the metal in the porphyrin ring. Four small sprigs of fresh parsley were chopped-up and a teaspoon volume taken by hand and gently rubbed onto the middle of two cotton fabric squares (3"×4") to give a green stain. To one of the stains were applied two drops of linoleic acid/surfynol mixture (2:1), which was then lightly rubbed with a glass rod to ensure all of the green stain was coated with the acid. The samples were then placed in an incubator (37° C.) and observed. Within minutes the green color was completely discharged to leave a colorless area where the green stain had been. This experiment demonstrates the metal center does not appear to play a role in the color discharge mechanism of linoleic acid.

EXAMPLE 10

Vitamin B12

Vitamin B12 is one of the essential vitamins required to sustain life, as it provides a vital biochemical role in the body. Chemically it also contains a porphyrin macrocyclic ring similar to hemoglobin and chlorophyll; but has cobalt in the center as opposed to iron or magnesium. A sample of vitamin B12 solution (1 mg/ml) was used in the following experiment. Two drops of the vitamin B12 solution were placed on each square (3"×3") of cotton fabric to yield a red spot. To one of the squares was placed two drops of a mixture of linoleic acid and surfynol (2:1) and gently rubbed with a glass rod to ensure complete coverage of the mixture across the red stain. The fabric samples were placed in an incubator (37° C.) and observed. Within minutes the red color of the treated stain largely discharged, leaving a pale yellow. Again, the identity of the metal in the center ring of the molecule appears not to alter the effectiveness of the decolorization mechanism.

EXAMPLE 11

Bilirubin

Bilirubin is a yellow breakdown product of normal heme catabolism in the body. Bilirubin reduction in the gut leads to a product called urobilinogen, which is excreted in the urine. It has the iron removed and the macrocyclic ring opened to give a tetrapyrrole linear molecule. Bilirubin is also further broken down in the intestine by the intestinal microbes via urobilin to a final product called stercobilin which gives feces the characteristic brown color.

Bilirubin was dissolved into water (30 mg/ml) and two drops were applied to two separate cotton squares. Then to one of the orange/yellow stains was applied a mixture of linoleic acid/surfynol (2:1) solution and spread across the stain by use of a glass rod. The samples were then placed into an incubator at 37° C. and the color was observed.

Within minutes the linoleic acid treated yellow stain color was discharged to leave a colorless area where the stain had been.

EXAMPLE 12

Iron 5,10,15,20-Tetrakis(pentafluorophenyl)-21H, 23H-phenylporphine ($FeTPF_5P$)

This fluorinated phenyl porphine contains iron in the center of the macrocylcic ring. It was selected as a model for the biological based porphyrin ring systems. It is not water soluble and a solution in acetonitrile was used to deliver the compound to the cotton fabric. Two drops of the porphine compound in actonitrile (30 mg/ml) were applied to the cotton fabric to give a brown stain. On one of the stains were applied two drops of the linoleic acid/surfynol solution, which sere then spread out with a glass rod to ensure complete coverage of the stain by the linoleic acid solution. The samples were placed into an incubator at 37° C. and observed. The brown stain was significantly reduced in color within minutes.

EXAMPLE 13

Copper 5,10,15,20-Tetraphenyl-21H,23H-porphine-o,o",o",o'"-tetrasulfonic acid, tetrasodium salt (CuT-$PPS_4$)

This porphine is another model system containing a copper metal ion in the center of the macrocyclic ring. The phenyl groups have one sulfonic acid group rendering the compound very water soluble.

Two drops of a solution of this porphine (30 mg/ml) was applied to two samples of cotton fabric. One of the stains had two drops of a solution of linoleic acid/surfynol applied and spread across the stain to ensure complete coverage of the stain by the solution. The samples were then placed in an incubator at 37° C. and observed. No significant color loss was observed even after the sample was incubated overnight (14 hrs). It is not yet clear whether the copper or the sulfonic acid substituted phenyl groups play a role in the stability of this porphine to the action of the linoleic acid system.

EXAMPLE 14

Carotene

While carotene, the main colorant in carrots, tomatoes and other orange/red fruits and vegetables, is not structurally related to porphine, it is a linear polyunsaturated molecule. It was unclear whether the linoleic acid system would discharge the orange color of carotene. A solution of carotene (30 mg/ml) in chloroform was placed onto square samples of cotton fabric. Onto one of the orange stains were placed two drops of the linoleic acid/surfynol mixture and spread via a glass rod to ensure coverage of the stain by the solution. The samples were then placed in an incubator at 37° C. and the color observed. While the color was not discharged within minutes, it was essentially discharged after 5 hours. This observation is helpful in solving the mechanism of action. Other polyunsaturated colored species will be examined later.

6. Role of Linoleic Acid and Other Fatty Acids

The surfactant type does not play a role in the color discharge mechanism, since it appears that any surfactant can be used. Surfynol, Tween, and Triton have all successfully been used as surfactants in the experiments with this system. The role of the surfactant is simply to lyse the blood cells in order to allow the fatty acids to gain access to and discharge the color of the hemoglobin. This was demonstrated in the experiment described above in which linoleic acid alone resulted in discharge of the red color of pure hemoglobin without the aid of a surfactant. However, the mechanism by which linoleic acid decolorizes the various compounds reported here is still unclear.

As mentioned, initial studies demonstrated that a mixture of surfactant with linoleic acid or linolenic acid discharged the red color of blood. Natural safflower and pumpkin seed oils, which contain significant quantities of linoleic acid, were also demonstrated to also remove the color of blood in the presence of a surfactant. To help elucidate the mechanism of decolorization, an experiment was conducted using stearic acid instead of linoleic, and it was observed that stearic acid did not discharge the red color of hemoglobin.

The fact that stearic acid did not discharge the color of hemoglobin points to an important role of the double bonds in both linoleic (2 double bonds) and linolenic (3 double bonds) acids in the mechanism of action. These fatty acids have been reported in the literature to undergo auto-oxidation forming cyclic peroxides. It is possible that hemoglobin provides the oxygen to catalyze the process, but it is unclear what happens to the hemoglobin to render it colorless rather than the expected green, brown or black which occurs with oxidation by other chemical oxidants.

7. Color Discharge of Melanin

EXAMPLE 15

Melanin is the brown pigmentation of the skin that is observed as freckles or aging spots (also known as liver spots). It is a complex colored macrocyclic. Experiments were run to determine if the fatty acid-based mixture would be able to discharge the color of melanin. A mixture of melanin in acetonitrile (7% wt/wt) was placed onto the cotton fabric (20 μl) and allowed to soak in and aircry to give a dark brown spot on the fabric. Next 200 μl aliquot of the linoleic acid/surfynol mixture (5:1 with surfynol being a 20% solution in water) was placed onto the stain and the liquid rubbed with the end of a glass rod to ensure coverage of the stain area. The fabric was then placed into an incubator at 37° C. and observed. The color was visually observed to decrease slowly in color as compared to the control. Full color discharge was reached after 3 days. This shows that the potential use of this linoleic acid-based composition for skin pigmentation remediation is possible.

8. Teeth Brightening and Stain Removal

EXAMPLE 16

Four previously extracted wisdom teeth were used in the study. All the teeth had yellow plaque, brown staining and dried blood on them. Two of the teeth were selected at random and each placed into 3 ml of a linoleic acid/surfynol mixture (5:1 where the surfynol was a 20% wt/wt solution in water) to which was also added urea peroxide to give the overall concentration of 0.3% wt./wt. The teeth therefore were submersed in this liquid. After 3 minutes the teeth were removed and rinsed under cold water and then placed on a towel to be visually compared with the control untreated teeth. It was quite striking to see the contrast. The plaque, stains and dried blood on the treated teeth were gone and no trace could be observed. In addition the teeth were whiter than the controls. It was clear that the linoleic acid-based mixture can be effectively and efficiently used as a teeth stain remover and brightening agent.

9. Kinetics of the Reaction and Role Oxidant as a Catalyst for the Linoleic Acid

EXAMPLE 17

We applied 50 μl of 7% wt/wt hemoglobin in water solution to cotton fabric squares and allowed the hemoglobin to soak into the fabric, creating a brown/red stain. Onto one stain is placed 200 μl of linoleic acid/Surfynol mixture (5:1 where surfynol was a 20% wt/wt solution in water) and briefly rubbed with the tip of a glass rod to ensure coverage of the stain. The hemoglobin color was fully discharged in about 2.4 minutes. Onto a second stain is placed 200 μl of a linoleic acid/surfynol (20% sulfynol in water)/urea peroxide solution (5:1:0.3) and briefly rubbed with the end of a glass rod to ensure coverage of the stain. The color was completely discharged in 34 seconds.

The color discharge role of the small amount of urea peroxide was tested. Thus, 200 μl sample of 0.3% wt/wt urea peroxide in water was applied to an identical hemoglobin stain and rubbed with the tip of a glass rod to ensure coverage of the stain. A slight dilution of the stain color was observed the stain persisted. Even after about 5 hours the vivid brown/red stain was still clearly visible to the unaided eye. Therefore urea peroxide alone does not discharge the color of the stain; rather it can be the catalyst for the linoleic acid mechanism.

10. CEILAB Measurement of Color Discharge

EXAMPLE 18

In order to quantify the magnitude of the color change a Minolta Spectrophotometer model CM-2600d was used to measure the color difference before and after discharge. The color difference of the samples in Example 17 is measured. ΔE of the stain color reduction of the Ilinoleic acid/surfynol sample after discharge of hemoglobin stain=35.5; ΔE of the stain color reduction of the linoleic acid/surfynol/urea peroxide sample after discharge of stain=49.6; ΔE of the stain color decrease using the urea peroxide solution sample=8.9.

The present invention has been described both in general and in detail by way of examples. Persons skilled in the art will understand that the invention is not limited necessarily to the specific embodiments disclosed. Modifications and variations may be made without departing from the scope of the invention as defined by the following claims or their equivalents, including equivalent components presently known, or to be developed, which may be used within the scope of the present invention. Hence, unless changes otherwise depart from the scope of the invention, the changes should be construed as being included herein.

We claim:

1. A composition for discharging blood stains, the composition comprising: an aqueous or other polar solvent-based solution containing about 0.01% to about 95% by volume of a unsaturated aliphatic acid or ester, said aliphatic acid or ester molecule having a carbon chain of at least $C_8$ or greater, and more than one carbon-carbon double bond; an oxidative catalyst; and a cell-lysing agent, wherein said unsaturated aliphatic acid or ester and cell lysing agent, when present, are present in amounts expressed as a ratio ranging from about 1:1 up to about 30:1, respectively.

2. The composition according to claim 1, wherein said carbon double bonds are conjugated.

3. The composition according to claim 1, wherein said oxidative catalyst is an oxidizing agent, a peroxide or cyclic peroxide molecule.

4. The composition according to claim 3, wherein said oxidizing agent is present in an amount from about 0.02% to about 1% by volume.

5. The composition according to claim 1, wherein said aliphatic acid or ester includes at least one of the following: linoleic acid; alpha-linolenic acid; eicosadienoic acid; eicosatrienoic acid; arachidonic acid (also known as eicosatetraenoic acid); eicosapentaenoic acid; or docosahexaenoic acid.

6. The composition according to claim 1, wherein the unsaturated aliphatic acid is present as an ester component of natural seed oils.

7. The composition according to claim 6, wherein the natural seed oil is selected from safflower, grape or pumpkin or soybean, or linseed, or peanut, or poppy, or perilla or a mixture thereof.

8. The composition according to claim 1, wherein said cell lysing agent is selected from a surfactant, alcohol, base, self-heating agent, quaternary ammonium compounds, and non-isotonic solutions.

9. The composition according to claim 1, wherein said unsaturated aliphatic acid or ester and cell lysing agent are present in amounts expressed as a ratio ranging from about 1:5 up to about 25:1, respectively.

10. The composition according to claim 1, wherein said unsaturated aliphatic acid or ester and cell lysing agent are present in amounts expressed as a ratio ranging from about 1:7 up to about 20:1, respectively.

11. The composition according to claim 1, wherein said blood stain is discharged within a period of about 60 minutes or less.

12. The composition according to claim 11, wherein said blood stain is discharged within about 15 minutes.

13. The composition according to claim 11, wherein said blood stain is discharged within about 3 minutes.

14. The composition according to claim 1, wherein the color of the stain is reduced by a ΔE of ≥5.

15. The composition according to claim 1, wherein the color of the stain is reduced by at least a ΔE value of 20.

16. The composition according to claim 1, wherein said composition is embodied in an aerosol, a liquid, a gel, a paste, or a solid form.

17. The composition according to claim 16, wherein said gel or solid form is either shear thinning or temperature responsive, which transforms to a liquid during application.

18. The composition according to claim 1, wherein said composition is used on surfaces of woven and nonwoven fabrics, clothing, skin, fur, carpet, walls, enamel, glass, metal, or agar and growth media.

19. The composition according to claim 1, wherein said composition discharges the color of blood or menses.

20. The composition according to claim 1, wherein said composition is used in bandages, medical patches, wraps, personal absorbent articles, medical drapes, meat trays and pads, and garments.

21. A blood stain-fighting product comprising:

an aqueous or polar-solvent based solution of polyunsaturated fatty acids and a cell-lysing agent in amounts expressed as a ratio ranging from about 1:5, up to about 30:1 respectively; and an oxidizing agent in an amount of 0.02% to 1% by volume, and which produces an observable color change in which a stain is reduced by at least a ΔE value of 5.

22. The stain-fighting product according to claim 21, wherein said oxidizing agent includes either peroxide or cyclic peroxide molecules.

23. The stain-fighting product according to claim 22, wherein said oxidizing agent is present in an amount from about 0.15-0.55% by volume.

24. The stain-fighting product according to claim 21, wherein said polyunsaturated fatty acid includes at least one of the following: a) linoleic acid ($C_{18}$:2); b) alpha-linolenic acid ($C_{18}$:3); c) arachidonic acid ($C_{20}$:4); d) eicosapentaenoic acid ($C_{20}$:5); docosahexaenoic acid ($C_{22}$:6); eicosadienoic acid ($C_{20}$:2); f) eicosatrienoic acid ($C_{20}$:3); g) a combination thereof.

25. The stain-fighting product according to claim 21, wherein said fatty acids are present as esters of alkyl alcohols (C1-C8), cyclic aliphatic alcohols, aromatic alcohols, glycerides, glycols (diols), polyvinyl alcohols, or polyethers.

26. The stain-fighting product according to claim 21, wherein said cell-lysing agent includes a surfactant.

27. The stain-fighting product according to claim 21, wherein said fatty acids and cell lysing agent are present in amounts expressed as a ratio ranging from about 1:7 up to about 25:1, respectively.

28. The stain-fighting product according to claim 21, wherein said surfactant is present at about 1-10% concentration, or 5-20% by volume of polyunsaturated aliphatic acid or ester.

* * * * *